US00PP23538P3

(12) United States Plant Patent
Hasegawa

(10) Patent No.: US PP23,538 P3
(45) Date of Patent: Apr. 16, 2013

(54) CARNATION PLANT NAMED 'CFPC MANA'

(50) Latin Name: *Dianthus caryophyllus*
Varietal Denomination: CFPC Mana

(75) Inventor: Oscar Hasegawa, Salinas, CA (US)

(73) Assignee: Snow Brand Seed Co., Ltd., Sapporo, Hokkaido (JP)

( * ) Notice: Subject to any disclaimer, the term of this patent is extended or adjusted under 35 U.S.C. 154(b) by 448 days.

(21) Appl. No.: 12/807,547

(22) Filed: Sep. 8, 2010

(65) Prior Publication Data

US 2012/0060250 P1 Mar. 8, 2012

(51) Int. Cl.
*A01H 5/00* (2006.01)

(52) U.S. Cl. ..... Plt./277

(58) Field of Classification Search ..... Plt./277
See application file for complete search history.

(56) References Cited

U.S. PATENT DOCUMENTS

PP17,596 P3 4/2007 Hasegawa ..... Plt./276

*Primary Examiner* — Annette Para
(74) *Attorney, Agent, or Firm* — Phase M, LLP

(57) ABSTRACT

A new variety of carnation plant named 'CFPC Mana,' having a compact form of plant with well presented dark pink flowers.

1 Drawing Sheet

Latin name of the genus and species: Botanical classification: *Dianthus caryophyllus.*

Variety denomination: The new carnation variety denomination is 'CFPC Mana".

BACKGROUND OF THE INVENTION

The present invention comprises a new and distinct cultivar of hybrid carnation botanically known as *Dianthus caryophyllus,* and referred to by the cultivar name 'CFPC Mana'. The new variety, identified as selection no. 090169, originated from a cross made by Oscar Hasegawa in a controlled breeding program in Salinas, Calif.

The female parent of the new variety is known as the selection no. 080194 and the male parent is known as the selection no. 080196. The new variety 'CFPC Mana' has been asexually reproduced by vegetative side shoot cuttings in Salinas, Calif. and the distinguishing characteristics are retained through successive generations of asexual reproduction.

BRIEF SUMMARY OF THE INVENTION

'CFPC Mana' is a potted spray-type carnation plant variety having a compact form of plant with well presented dark pink flowers.

Comparison With Female Parent

Plants of the new carnation variety 'CFPC Mana' are similar to the female parent selection no. 080194 in plant habit and growth rate. Under similar growing conditions in Salinas, Calif., under commercial practice, plants of the new carnation variety 'CFPC Mana' differed from plants of the female parent in the following characteristic:

1. The new variety 'CFPC Mana' produces dark pink flowers whereas the female parent selection no. 080194 produces lighter pink color flowers.

Comparison With Male Parent

Plants of the new carnation variety 'CFPC Mana' are similar to the male parent selection no. 080196 in plant habit and growth rate. Under similar growing conditions in Salinas, Calif., under commercial practice, plants of the new carnation variety 'CFPC Mana' differed from plants of the male parent in the following characteristic:

1. The new variety 'CFPC Mana' produces pink flowers whereas the male parent selection no. 080196 produces darker pink flowers.

Comparison With Other Similar Varieties

Plants of the new carnation variety 'CFPC Mana' are similar to plants of the variety 'CFPC Annette' (U.S. Plant Pat. No. 17,596) in plant habitat and growth rate. Under similar growing conditions, however, in Salinas, Calif., under commercial practice, plants of the new carnation variety 'CFPC Mana' differed from plants of 'CFPC Annette' in the following characteristic:

1. The flower color of the new variety 'CFPC Mana' is a darker pink than the flower color of 'CFPC Annette'.

BRIEF DESCRIPTION OF ILLUSTRATION

Typical specimens of the plant and flowers for the new carnation variety 'CFPC Mana' are shown in the accompanying photograph. The colors shown are as true as possible within the usual limits of this kind of illustration.

FIG. 1 is a whole plant view of the new variety 'CFPC Mana' grown in a pot.

The plant shown in the illustration is 139 days from date of planting.

DETAILED BOTANICAL DESCRIPTION

The following description of the new carnation variety 'CFPC Mana' is of plants 139 days from a planting date of Dec. 6, 2009, grown in a commercial greenhouse in Salinas, Calif. The cultivar has not been observed under all possible environmental conditions. The phenotype may vary significantly with variations in the environment such as temperature, length of day and light intensity without any variance in genotype.

Plants of the new variety have been grown successfully under temperature conditions averaging about 18° C. at night and about 24° C. to 28° C. during the day under light conditions of about 14 hours. Plants are daylight neutral and flower throughout the year. Chemical growth regulators are not required for production. The new variety may be produced as a potted spray-type carnation. To produce a commercial product the plants may be pinched once with the center bud removed. Pinched plants are about 7 inches tall and about 7 inches in diameter. Flower diameter averages about 2 inches with a crown of about 1 inch. Foliage is generally about 3 inches long and about ¼ inches at the widest point. The typical container size for commercial growth is 4½ inches.

It has been observed that the shelf life of the new variety is about 26 days with a time to first bud opening of about 15-16 weeks. The commercial classification of the new carnation variety is a potted spray-type. The plant hardiness zone has not been determined.

The following description is with respect to a plant produced as a potted spray-type carnation. The plant and flower measurements and foliage size are established as an average using standard commercial cultural practices. In the description of this new carnation variety, color values have been taken from The Royal Horticultural Society Colour Chart (R.H.S.C.C.).

Plant

Height (inches): 7.
Form: Herbaceous.
Growing habit: Semi upright.
Branching characteristics: 3-4 laterals per stem.
Breaking action: 6-7 breaks per plant with strong straight stems.
First appearance of color in buds: 105 days after planting.
Vigor: Excellent.
Shelf life: 26 days.
Blooming habit: Spray type.
Blooming season: Year round.
Lastingness of blooms: About 14 days.
Disease (susceptibility/resistance observed): Excellent resistance to soil-borne diseases such as *Fusarium oxysporum* and *F. graminearium,* and root rots such as damping off, water molds and similar types, as are typical of carnations.
Pest susceptibility/resistance: Not evaluated or observed.
Drought and temperature susceptibility/resistance: Not evaluated or observed.
Mutation prone: No.
Propagation:
- *Type*.—Side shoot cuttings.
- *Time to rooting*.—18 days with soil temperatures of about 18° C. to 21° C.
- *Rooting habit*.—Good fibrous system.

Growth treatments or special conditions: Single pinch.

Foliage

Stem:
- *Length* (*inches*).—6.
- *Diameter* (*inches*).—¼ (at base).
- *Texture*.—Smooth.
- *Cross section*.—Edged.
- *Color*.—141-A internode. 143-D node.

Number of leaves per lateral branch: 28.
Arrangement of leaves: Bi-lateral along the stem.
- *Shape of leaf*.—Long, narrow, lanceolate.
- *Size of leaf*.—Width (inches): ¼. Length (inches): 3.
- *Leaf apex*.—Acute.
- *Edge*.—Smooth.
- *Base*.—Smooth.
- *Aspect*.—Elliptie.
- *Surface texture*.—Top: smooth. Bottom: smooth.

Leaf venation: Prominent mid-vein at underside.
Leaf longitudinal axis: Recurbed.
Leaf cross section (upper side): Weakly concave.
Leaf color:
- *Mature leaf*.—Upper side: 137 A; under side: 137 B.
- *Young leaf*.—Upper side: 137 D; under side: 138 A.

Leaf waxy layer: Medium.

Flower

Flower appearance: Matte to shiny.
Flower type: Single/double.
Flower profile of upper part of corolla: Convex.
Flower profile of lower part of corolla: Flat convex.
Flower shape: Somewhat domed shape rounded.
Number of blossoms per branch: 5.
- *Depth of fully expanded blossoms* (*inches*).—1.
- *Diameter of fully expanded blossoms* (*inches*).—2.

Calyx:
- *Sepals number*.—5.
- *Length* (*inches*).—1.
- *Width* (*inches*).—½.
- *Color*.—Outer side base: 138 C. Outer side middle to tip: 141 B. Inner side: 138 D.
- *Texture*.—Smooth.
- *Appearance*.—Matte with waxy bloom.
- *Shape*.—Cylindrical.

Flower petals:
- *Form/shape*.—Fan shape.
- *Petal edge*.—Serrated: width: 1/16 inch. Depth: 1/16 inch. Edge type: crenate-dentate.
- *Texture*.—Smooth.
- *Appearance*.—Matte-shiny.
- *Petal surface of blade*.—Undulating.
- *Number per flower*.—28.
- *Outer petals*.—Length (inches): 2. Width (inches): 1¼.
- *Inner petals*.—Length (inches): 1½. Width (inches): 1.

Fragrance: Absent.
Flower bud (at onset of color):
- *Length* (*inches*).—1½.
- *Diameter* (*inches*).—½.
- *Form/shape*.—Cylindrical.

Flower color:
1. *General tonality*.—Dark pink.
2. *Petals, upper surface*.—57 B.
3. *Petals, lower surface*.—57 C.
4. *Petals, edge*.—57 A.
5 *Petals, center*.—57 B.
6. *Early bud*.—57 A.

Petal macule (random spots): Absent.
Flower progression with age: Color fades very slightly to lighter color.

Reproductive organs

Gynoecium: Pistillate.
- *Pistil number*.—1.

*Pistil length* (*inches*).—1.

*Stigma color*.—65 D — white with pink.

*Stigma shape*.—Filamentous.

*Style color*.—Whiter than 155 D.

*Style length* (*inches*).—1½.

*Style number*.—Two and three.

Ovary:

*Shape*.—Ovoid.

*Surface*.—Smooth.

*Color*.—Base: 155 D. Body: 145 C. Apex: 143 A.

Androecium: None produced.

Fruit and seeds: None produced.

What is claimed is:

1. A new and distinct variety of carnation plant, substantially as described and illustrated herein.

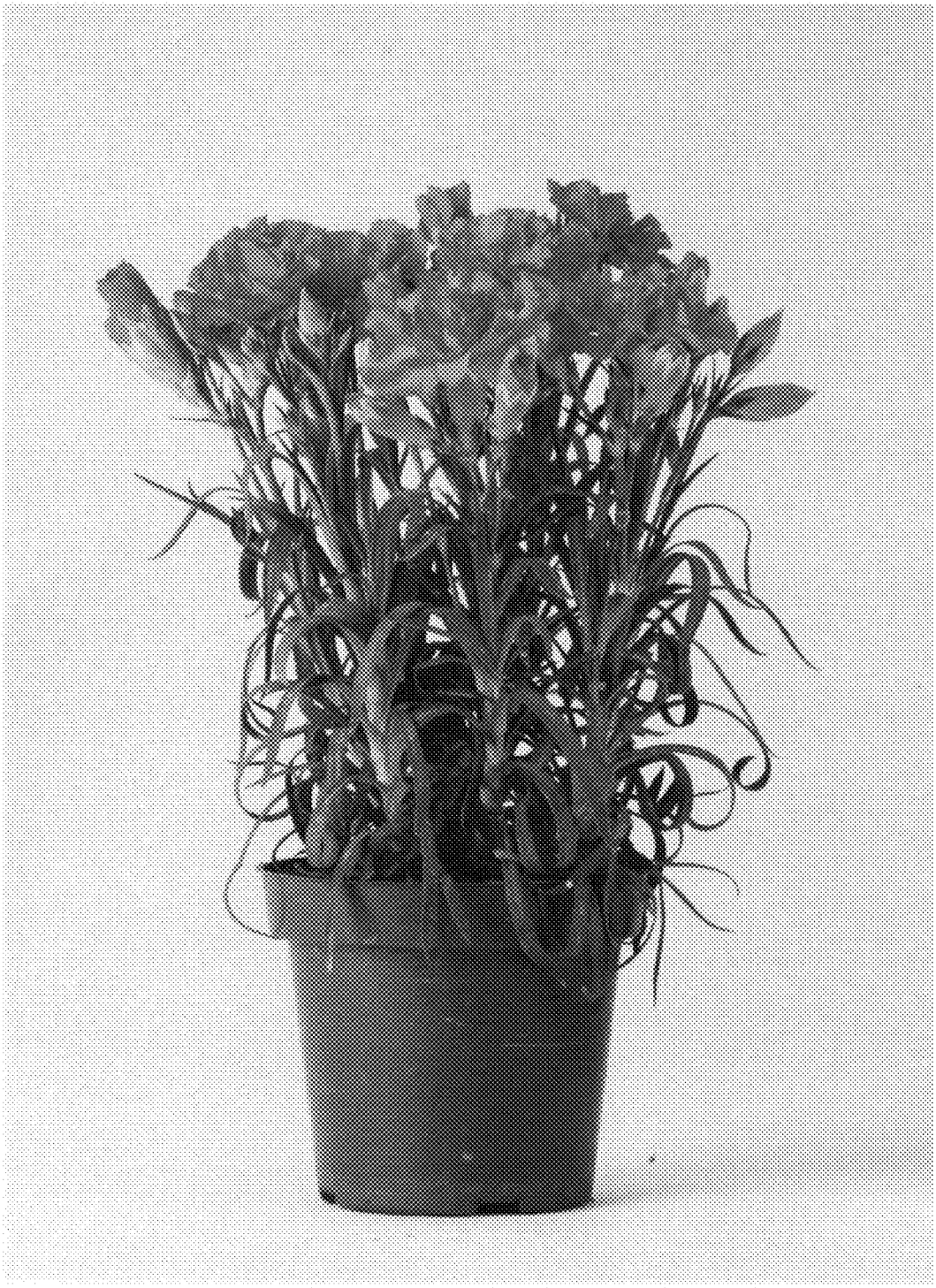

* * * * *